United States Patent
Jones et al.

(10) Patent No.: US 9,480,603 B2
(45) Date of Patent: Nov. 1, 2016

(54) SYSTEMS AND METHODS FOR LASER CORRECTION OF ASTIGMATISM INCIDENT WITH LENS REPLACEMENT SURGERY

(71) Applicant: LaserArcs, LLC, Swansea, IL (US)

(72) Inventors: Bart A. Jones, Caseyville, IL (US); Michael P. Jones, Belleville, IL (US)

(73) Assignee: LASERARCS, LLC, Swansea, IL (US)

( * ) Notice: Subject to any disclaimer, the term of this patent is extended or adjusted under 35 U.S.C. 154(b) by 571 days.

(21) Appl. No.: 13/795,084

(22) Filed: Mar. 12, 2013

(65) Prior Publication Data

US 2014/0276675 A1    Sep. 18, 2014

(51) Int. Cl.
*A61F 9/008*    (2006.01)

(52) U.S. Cl.
CPC .. *A61F 9/00827* (2013.01); *A61F 2009/00859* (2013.01); *A61F 2009/00872* (2013.01); *A61F 2009/00887* (2013.01)

(58) Field of Classification Search
CPC ............ A61B 3/00; A61B 3/10; A61B 3/16; A61B 3/103; A61B 3/107; A61B 18/18; A61F 2/14; A61F 9/00; A61F 9/007; A61F 9/008
USPC ..................... 606/2, 107, 166; 607/2, 80, 88
See application file for complete search history.

(56) References Cited

U.S. PATENT DOCUMENTS

2008/0312675 A1*  12/2008  Newcott ................. A61F 9/008
                                                                  606/166

OTHER PUBLICATIONS

Richard M. Awdeh, Hewitt Hanafee, Ana-Paula Canto, Using a Laser for Arcuate Incisions, Cataract & Refractive Surgery Today, Cover Story, Sep. 2011.*
J. E. McDonald, A look at limbal-relaxing incisions, EyeMail Insights, May 2006.*
Louis D. Nichamin, Modified Astigmatism Correction Nomogram, Journal of Refractive Surgery, vol. 24, p. 562-563, Jun. 2008.*
Louis D. Nichamin, Corneal Relaxing Incisions, Cataract & Refractive Surgery Today, Cover Story, p. 57-60, May 2006.*
Hurmeric et al, Femtosecond-Assisted Astigmatic Keratotomy, Cataract & Refractive Surgery Today Europe, Oct. 2010.*
"DONO-Donnefeld Nomogram," Abbott Medical Optics Inc.—LRI Calculator, http://www.lricalculator.com, 2010, one page.
"NAPA-Nichamin Nomogram," Abbott Medical Optics Inc.—LRI Calculator, http://www.lricalculator.com, 2010, one page.

* cited by examiner

*Primary Examiner* — Gary Jackson
*Assistant Examiner* — Qingjun Kong (57) ABSTRACT

A nomogram, a method for determining how to cut a cornea to produce a particular vision correction, and a system and method for determining how to make a vision correction when a precision cutting tool is being used as opposed to the performance of hand cuts. In a further embodiment, measurement of astigmatism to be corrected, calculation of the nomogram, and the actual cutting are mostly or completely automated eliminating human error from the system.

13 Claims, 8 Drawing Sheets

Vertical (70°-110°)

|       | 0.5-0.59 | 1.0-1.09 | 1.5-1.59 | 2.0-2.09 | 2.5-2.59 | 3.0-3.09 | 3.5-3.59 | 4.0+ |
|-------|----------|----------|----------|----------|----------|----------|----------|------|
| 20-39 | 30       | 45       | 55       | 68       | 80       | >90      | >90      | >90  |
| 30-39 | 28       | 42       | 52       | 65       | 78       | 90       | >90      | >90  |
| 40-49 | 25       | 40       | 50       | 62       | 75       | 88       | >90      | >90  |
| 50-59 | 22       | 38       | 48       | 60       | 72       | 85       | >90      | >90  |
| 60-69 | 20       | 35       | 45       | 58       | 70       | 82       | >90      | >90  |
| 70-79 | 18       | 32       | 42       | 55       | 68       | 80       | >90      | >90  |
| 80-89 | 15       | 30       | 40       | 52       | 65       | 78       | 90       | >90  |
| 90+   | 1 @ 25   | 28       | 38       | 50       | 62       | 75       | 88       | >90  |

FIG. 6A

Oblique (21°-69° and 111°-159°)

|       | 0.5-0.59 | 1.0-1.09 | 1.5-1.59 | 2.0-2.09 | 2.5-2.59 | 3.0-3.09 | 3.5-3.59 | 4.0+ |
|-------|----------|----------|----------|----------|----------|----------|----------|------|
| 20-39 | 25       | 38       | 50       | 62       | 75       | 88       | >90      | >90  |
| 30-39 | 22       | 35       | 48       | 60       | 72       | 85       | >90      | >90  |
| 40-49 | 20       | 32       | 45       | 58       | 70       | 82       | >90      | >90  |
| 50-59 | 18       | 30       | 42       | 55       | 68       | 80       | >90      | >90  |
| 60-69 | 15       | 28       | 40       | 52       | 65       | 78       | 90       | >90  |
| 70-79 | 1@25     | 25       | 38       | 50       | 62       | 75       | 88       | >90  |
| 80-89 | 1@22     | 22       | 35       | 48       | 60       | 72       | 85       | >90  |
| 90+   | 1@20     | 20       | 32       | 45       | 58       | 70       | 82       | >90  |

FIG. 6B

Horizontal (160°-20°)

|       | 0.5-0.59 | 1.0-1.09 | 1.5-1.59 | 2.0-2.09 | 2.5-2.59 | 3.0-3.09 | 3.5-3.59 | 4.0+ |
|-------|----------|----------|----------|----------|----------|----------|----------|------|
| 20-39 | 1@32     | 28       | 36       | 46       | 54       | 64       | 76       | 86   |
| 30-39 | 1@30     | 26       | 35       | 45       | 52       | 62       | 74       | 84   |
| 40-49 | 1@28     | 25       | 34       | 44       | 51       | 60       | 72       | 82   |
| 50-59 | 1@26     | 24       | 32       | 42       | 49       | 58       | 70       | 80   |
| 60-69 | 1@25     | 24       | 32       | 42       | 49       | 58       | 70       | 80   |
| 70-79 | 1@25     | 23       | 30       | 40       | 46       | 56       | 66       | 76   |
| 80-89 | 1@24     | 22       | 28       | 38       | 44       | 54       | 64       | 74   |
| 90+   | 1@22     | 19       | 26       | 36       | 42       | 52       | 62       | 72   |

SYSTEMS AND METHODS FOR LASER CORRECTION OF ASTIGMATISM INCIDENT WITH LENS REPLACEMENT SURGERY

BACKGROUND

1. Field of the Invention

This invention relates in general to the use of femtosecond lasers to produce corneal cuts in the correction of astigmatism and more particularly to the generation of a nomogram for directing a femtosecond laser for making such cuts in conjunction with lens replacement surgery.

2. Description of the Related Art

Cataracts are areas of opacification of the lens of the eye of sufficient size to interfere with vision. They have been extensively studied because of their high prevalence in the elderly. Cataracts in the elderly (senile cataracts) are the most common type, and are often thought to be due to an acceleration of the scattering of light as it passes through the lens. Cataracts occur to varying extents in all humans over the age of 50, but generally do not cause significant visual problems until the ages of 60-80 years. In some instances, however, cataracts can occur much earlier as a result of risk factors including congenital disease, trauma, and family history.

Generally, correction of an occurrence of cataracts in an individual requires surgical intervention. In the surgical correction of the lens, an optical surgeon will make two relatively small incisions through the cornea of the eye at generally 90 degrees from each other. The major incision being on the outside of the cornea with the other being positioned based on the handedness of the surgeon. The surgeon will then remove the natural lens with the cataract, and replace the lens with an artificial lens. The incisions can then be sutured or otherwise closed, and the eye is allowed to heal.

Because cataract surgery involves replacement of the natural lens with an artificial lens, there is a side benefit to cataract surgery. Focal errors in the natural lens can be corrected through the correct selection of an artificial lens. Specifically, if a person was nearsighted (myopic) due to a focal length issue caused by the natural lens focusing light in the eye in front of the retina, the replacement lens can be selected to have a longer focal length than the natural lens that was removed. The person recovering from cataract surgery may have better vision than they did before getting cataracts as the focal point is now correctly on the retina. A similar choice of lens can be made to shorten the focal length if the person is farsighted (hyperopic). In effect, correction of cataracts can correct other problems with vision which may have nothing to do with the cataract itself.

As part of this additional vision correction, some patients would like to not just have better vision from cataract surgery, but to have good enough vision that they no longer need to wear corrective lenses. As surgical methods to improve sight, such as laser-assisted in situ keratomileusis, or LASIK, have become more common, the need for eye surgery (which is often a scary proposition) now often brings with it a desire to correct everything at once and patients who are undergoing eye surgery often desire to come out of it with perfect vision, regardless of the reason it was needed in the first place.

While a replacement lens can correct a number of focal problems from myopia or hyperopia, specifically, the lens can be chosen to be a lens which may have a different focal distance from the natural lens in order to correct focal imbalances between the natural lens and the cornea, it cannot correct all vision problems. Specifically, the replacement lens is essentially a perfect lens. Thus, patients who have focal problems that are not due to the focal length of their cornea and lens combination, but have focal problems due to focal imperfections in the cornea causing distortion, the lens replacement may not only fail to correct vision, but could make it worse. The most common visual impairment of this type is astigmatism, the condition where the lens is not symmetric but is squashed or bowed along a particular axis.

It is known that cutting incisions in the cornea which are then allowed to heal can result in alteration of the shape of the cornea and that such alterations can be beneficial in improving focal problems with the eye. The radial keratotomy procedure utilized this exact type of cuts to reshape the cornea and LASIK is essentially an improved technique on the same type of procedure. While this can be used to reshape the cornea to result in repositioning of the focal point (as is done in LASIK), it can also be used to correct for astigmatism by causing the cornea to heal in a fashion that regains a target shape from its squashed shape.

When it comes to astigmatism, the surgical procedure to replace a lens often induces a slight astigmatism (or may correct an existing astigmatism) by the very need to cut through the cornea to access the lens. This "induced" astigmatism, and the ability to provide additional correction at the same time, has led to astigmatism correction often being performed simultaneous to a lens replacement to help improve vision. While the correction can be performed via LASIK, such a major procedure is generally not needed and therefore astigmatism correction in conjunction with lens replacement is often a much simpler procedure.

Traditionally, the modification of the eye to reduce astigmatism is performed by performing one or more arcuate cuts towards the peripheral part of the cornea. These cuts are generally not all the way through the cornea, but only part way to allow for the cornea to alter its relative pressure and reshape without being fully penetrated. Obviously, correction of an astigmatism requires that the cuts be both correctly positioned (generally along the long axis of the astigmatism) and the correct length and depth to result in the correct reshaping from the more parabolic arc of an astigmatic eye, to the more hemispheric arc that is normal.

In order to know how to perform the cuts, doctors have relied for many years on nomograms, which are essentially cutting maps. These can be generated from hand calculations or from websites such as www.lricalculator.com where a doctor can enter the specifics of a patient's eye and be provided with the locations and size of cuts to be performed.

These websites and systems, however, suffer from a couple of major flaws. For one, the calculations are necessarily crude and lack detail. A human is simply incapable of cutting an arc of 24.6° consistently and therefore the nomograms tend to have a roughness with values provided in 5° arcs to take into account a surgeon's slop in simply not being able to make the correct sized cuts. Further, while cuts are supposed to be to a fixed depth, the depth of a cornea is often not known in a hand surgical procedure, and even if it is and a guarded blade of fixed penetration is used, the cut may not actually follow the prescribed depth at all points due to variations in the structure of the cornea.

Because of the inherent "sloppiness" in the making of such cuts by hand, while a traditional nomogram can provide useful guidance to a surgeon, it is, in many respects, no better than an educated guess and a skilled surgeon could often make a fairly accurate correction even without knowing what size cut to make at all. Further, it is difficult, if not impossible, to verify the accuracy of current nomograms as results on two patients with an identical procedure being performed may be different simply due to the skill, and luck, of the doctor performing the procedure.

Traditional nomograms are often based on simple mathematical relationships with a few centrally defined charts and relationships. In many nomograms, the charts provide for generally linear or other relatively simple mathematical relationships between variables in the various dimensions. Generally, there are three variables that matter in selecting how big of a cut to make. These variables are: 1) The axis of the astigmatism, 2) the amount of the astigmatism, and 3) the age of the patient. While the need to understand the first two variables should be obvious, the third is desired as the cornea changes in flexibility over life and thus older patients' corneas generally need smaller cuts than younger patients.

While the process of hand cutting is necessarily fraught with human error, recent advances in computer controlled cutting implements, such as ultrafast laser knives like the femtosecond laser, have provided tools where the surgeon's skill (and luck) with a blade are removed. The laser can cut precise cuts over and over again with a level of precision that the human hand is simply incapable of replicating. This type of tool, therefore, shows huge promise in being able to make vision correction much more accurate.

However, the tool is only as good as the skill of one using it and while a femtosecond laser may be able to make precise cuts, a surgeon still needs to know where to make those cuts. Nomograms for hand cutting are not useful for such surgery as their assumed degree of slop, and their course measurement, render more noise than value when the cutting instrument is accurate.

SUMMARY

Because of these and other problems in the art, described herein, among other things, is a nomogram, a method for determining how to cut a cornea to produce a particular vision correction, and a system and method for determining how to make a vision correction, and then automatically instructing a cutting tool to do so.

The systems and method discussed herein are primarily for use in correcting astigmatism as a secondary surgical procedure incident to a lens replacement. While it should be recognized that the nomograms can be used to correct astigmatism as a primary surgery, such a surgery would be rarely performed as such correction can be performed already as part of LASIK and other vision correction surgery.

There is described herein, among other things, a method of cutting the cornea of an eye to correct astigmatism, the method comprising: determining an amount of astigmatism of the eye; determining an axis of the astigmatism of the eye; determining an age of the eye; selecting a mirrored cut position in the cornea, said cut position being less than a 10 mm optical zone and greater than a 6 mm optical zone and comprising two cuts on opposing sides of the eye; calculating a cut length from said amount, age, and cut position; and utilizing a precision cutting instrument to cut said cut length at said cut position.

In an embodiment of the method, said cut position is greater than an 8 mm optical zone.

In an embodiment of the method, said cut position is about 8 mm.

In an embodiment of the method, said cut position is about 9 mm.

In an embodiment of the method, said cut position is between 8 mm and 9 mm.

In an embodiment of the method, said cut position is between 9 mm and 10 mm.

In an embodiment of the method, said precision cutting instrument comprises a femtosecond laser.

In an embodiment of the method, if said axis is greater than 20° from the vertical and horizontal axis of said eye, said cut length is determined by the formula:

$$\text{cut length} = 60° - (5° - X) + (5° - Y);$$

where $$X = \frac{\text{number of patient's age in years} - 30}{20};$$

and $$Y = \frac{\text{number of patient's astigmatism in diopters} - 2}{0.2}.$$

In an embodiment of the method, if said axis is less than or equal to 20° from the vertical axis of said eye, said cut length is determined by the formula:

$$\text{cut length} = 65° - (5° - X) + (5° - Y);$$

where $$X = \frac{\text{number of patient's age in years} - 30}{20};$$

and $$Y = \frac{\text{number of patient's astigmatism in diopters} - 2}{0.2}.$$

In an embodiment of the method, said cut length is between 15° and 90°.

In an embodiment of the method, said method is performed in conjunction with surgery to replace a lens in said eye.

There is also described herein a method of cutting the cornea of an eye to correct astigmatism, the method comprising: determining an amount of astigmatism of said eye; determining an axis of the astigmatism of said eye; determining an age of said eye; calculating a cut length from said amount, age, and cut position; and utilizing a femtosecond laser to cut said cut length at said cut position; wherein said axis is at least 20° from the horizontal or vertical axis of said eye and wherein said cut length is determined by the following formula:

$$\text{cut length} = 60° - (5° - X) + (5° - Y);$$

where $$X = \frac{\text{number of patient's age in years} - 30}{20};$$

and $$Y = \frac{\text{number of patient's astigmatism in diopters} - 2}{0.2}.$$

In an embodiment of the method, said cut is one of a pair of mirrored cuts on opposing sides of said eye.

In an embodiment of the method, said cut length is between 15° and 90°.

In an embodiment of the method, said method is performed in conjunction with surgery to replace a lens in said eye.

There is also described herein, a method of cutting the cornea of an eye to correct astigmatism, the method comprising: determining an amount of astigmatism of the eye; determining an axis of the astigmatism of the eye; determining an age of the eye; calculating a cut length from said amount, age, and cut position; and utilizing a femtosecond laser to cut said cut length at said cut position; wherein said axis is no more than 20° from the vertical axis of said eye and wherein said cut length is determined by the following formula:

cut length=65°−(5°−$X$)+(5°−$Y$);

where $$X = \frac{\text{number of patient's age in years} - 30}{20};$$

and $$Y = \frac{\text{number of patient's astigmatism in diopters} - 2}{0.2}.$$

In an embodiment of the method, said cut is one of a pair of mirrored cuts on opposing sides of said eye.

In an embodiment of the method, said cut length is between 15° and 90°.

In an embodiment of the method, said method is performed in conjunction with surgery to replace a lens in said eye.

BRIEF DESCRIPTION OF THE DRAWINGS

FIG. 3 is for a vertical astigmatism (70°-110°).

FIG. 4 is for an oblique astigmatism (21°-69° or 111°-159°).

FIG. 5 is for a horizontal astigmatism (160°-20°).

DESCRIPTION OF PREFERRED EMBODIMENT(S)

This disclosure will discuss systems and methods for making cuts in the cornea of an eye, particularly a human eye, using a precise cutting tool. This tool will generally be a femtosecond laser but one of ordinary skill would understand that other precision blades may exist or be developed in the future. The key component of the precision knife is that it cuts precisely based on the material it is cutting. Thus, the dimensions of the cut are known to a high degree of accuracy. The cuts will generally be made to correct an astigmatism of the eye which is both naturally occurring and/or induced by a lens replacement procedure as a secondary operation performed with a lens replacement procedure. However, the procedure may be performed either alone, or with other procedures in alternative embodiments.

It should be recognized that while this disclosure will specifically describe the use of a femtosecond laser, the nomograms and methods discussed herein are applicable to any precise cutting instrument which is capable of making fine precise cuts in a repeatable fashion. It does not apply to the performance of such a procedure by hand as a human surgeon is simply incapable of cutting precisely enough for the nomogram to be of value.

Figure 1:
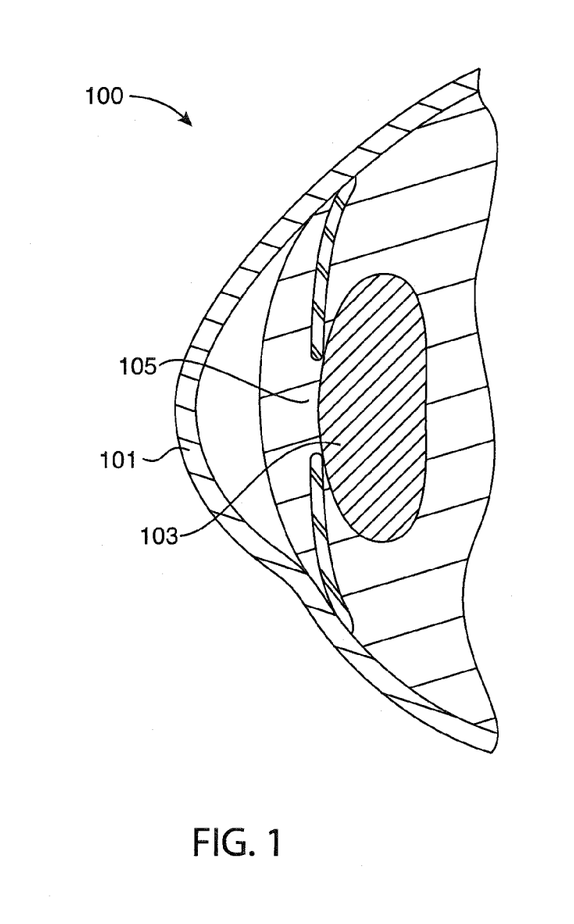
FIG. 1 provides a sectional view of a human eye.
Figure 2:
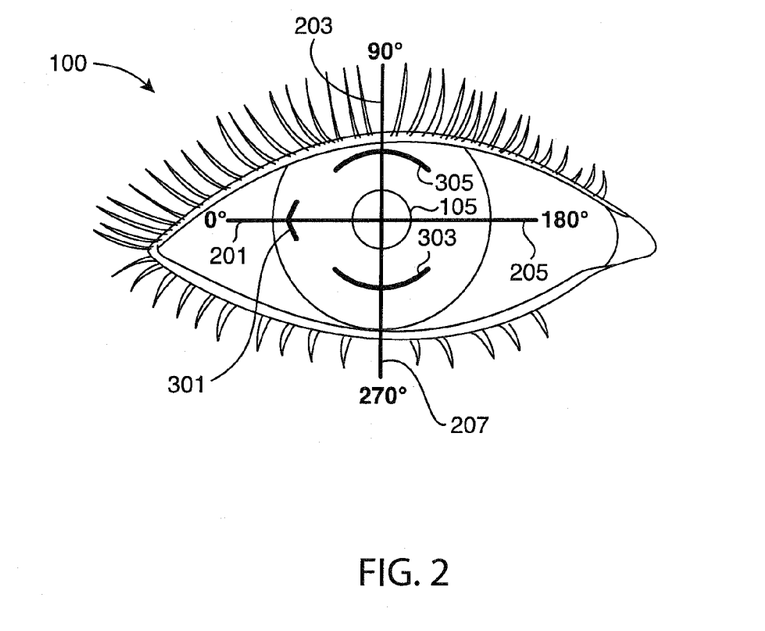
FIG. 2 provides a top view of a human eye illustrating coordinate system and cut positions for a vertical astigmatism.

FIG. 1 provides a sectional view of the eye (100) showing the cornea (101) and lens (103) which are the two primary focusing components of the eye (100). FIG. 2 provides a showing of a hypothetical nomogram for a particular astigmatism correction. In this case, the astigmatism is assumed to be vertical (the eye is taller than it is wide) which is commonly referred to as "with-the-rule" astigmatism.

In FIG. 2, there is shown the coordinate system as it is commonly used by an eye surgeon. The coordinate axis (which is rotational as opposed to x-y) is centered in the center of the pupil (105) with 0° (201) directed to the near side of the patient which is commonly where the surgeon will sit. 90° (203) is therefore toward the top of the patient's head, 180° (205) is toward the patient's other eye, and 270° (207) is toward the patient's feet. A first incision (301) is made generally centered at 0° in order to perform the lens implant.

In the depicted embodiment of FIG. 2, the incision (301) is at a 90 degree angle to the astigmatism (which is vertical or has a major axis along the vertical axes of the coordinate system in FIG. 2). Thus, this incision (301) will actually induce additional astigmatism. This incision (301), however, is necessary to perform the underlying procedure. The incision (301) will generally range from about 15° to about 45° and will fully penetrate the cornea (101) and may be performed by hand or with the use of the same precision cutting tool that will be used to correct the astigmatism. The latter is generally preferred as that makes this incision (301)

a precise size and, thus, the amount of astigmatism alteration that occurs because of it can be more precisely determined.

The remaining two cuts shown in FIG. 2 are the cuts (303) and (305) which are made to correct the astigmatism. In this case, both astigmatism that naturally occurs, and that which is induced by the surgical incision (301), is to be corrected. The cuts (303) and (305) are not complete incisions but will generally be made only a fixed percentage of the way through the cornea as this is all that is necessary to relieve pressure and cause the cornea to reshape. Specifically, the cuts will generally be 80% of the total thickness through the cornea, and will not cut either the inner or outer surface. In this way, the cuts (303) and (305) do not need to be sutured and will usually result in reduced pain. However, in an alternative embodiment, the outer surface of the cornea (101) may be cut through.

The inclusion of the incision (301) in the calculation of the nomogram is important as, since it is necessary to perform the underlying procedure, it will occur regardless. As the location of this incision (301) is generally fixed (it is always at the 0° position or the outermost point of the eye as this is usually the closest point to the physician performing the procedure and most convenient place), it is usually relatively easy to compensate for. In the event of horizontal astigmatism, this incision (301) will assist in correction. In a vertical astigmatism, this incision (301) will essentially create additional astigmatism. However, because the incision (301) is completely through the cornea (101), and is only on one side, it does result in some significant adjustment being required when correcting for horizontal astigmatism as will be discussed later.

For purposes of this disclosure, it is presumed that the astigmatism caused or corrected by the incision (301) is simply included in the astigmatism that needs to be corrected when the nomogram program is run. In this way, when this disclosure indicates the amount of astigmatism that needs to be corrected, that amount is presumed to include all induced astigmatism (or correction) from surgical necessity.

Because of the effect of the incision (301), the cuts (303) and (305) made specifically for astigmatism correction when astigmatism is in the horizontal axis are generally shorter than when the astigmatism is in the vertical axis (less correction is required) and it is, therefore, possible to correct greater astigmatism in the horizontal axis than in the vertical axis. Specifically, it is generally not recommended that the cuts made be too large. Thus, while it is possible, in theory, to correct any astigmatism, there is a practical limit.

Cuts (303) and (305) as discussed herein are generally described based on their length in degrees. This is done not only because it is a standard accepted methodology, but also because it provides for a determination of a fixed length which is the same regardless of the eye's physical size. To make a cut in degrees (as can be seen in FIG. 2), the cut (303) or (305) is centered at the target axis (which is the major axis of the astigmatism, the axis (203)-(207) in FIG. 2), and extends an equal length in each direction from that axis. With this positioning in mind, it should be clear that making cuts of greater than 90° (45° on either side of the axis) will result in the cut extending across the midline between the major and minor axis of the cornea (101) and thus, arguably, the healing of the cuts (303) and (305) can cause both reshaping in the desired dimension (the major axis), but also in the other direction (the minor axis). This dual reshaping can result in unpredictability in correction, and, thus, cuts (303) or (305) of greater than 90° are generally not used. In this case, the surgeon may make a 90° cut to correct as much of the astigmatism as possible, or may elect to not perform the astigmatism correction at all.

Further, the present case provides that there always be made two identical (mirrored) cuts (305) and (303) on either side of the eye (100), to the extent this is possible. It should be recognized that one can have generally the same effect by making a single cut that is twice as long on one side of the eye (100) as two shorter cuts on opposing sides of the eye (100). However, as the eye (100) is symmetrical, it is preferred that the cuts be made on opposing sides instead of just one. Nonetheless, even a femtosecond laser has an inherent limitation in that it cannot make very small cuts, and such small cuts will often heal without any reshaping. Thus, if the cuts (303) and (305) are going to be less than 15°, a cut of double the length is made on a single side of the eye. This is most common (as can be seen in the first column of FIG. 6C) for horizontal correction of a relatively small amount of astigmatism. In this case, the incision (301) is likely fully correcting (or even overcorrecting) the astigmatism and thus the single incision (which would be toward the nose or the 180° axis (205)) is used.

Figure 3:
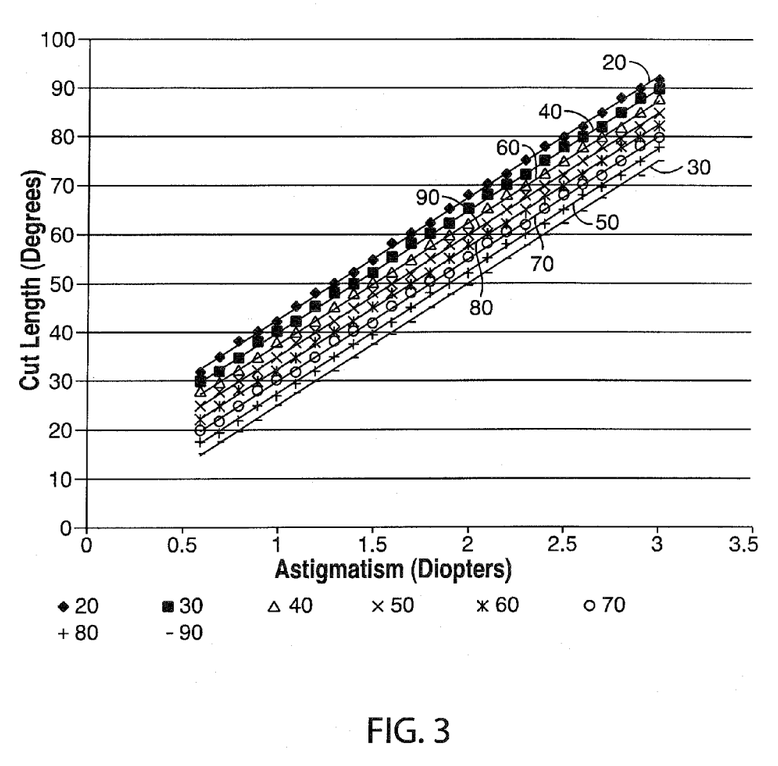
FIG. 3 provides a graph of the cut length (in degrees) based on the present astigmatism (in diopters) for patients in 8 different age ranges when performed in the 10 mm optical zone at 80% corneal depth.
Figure 4:
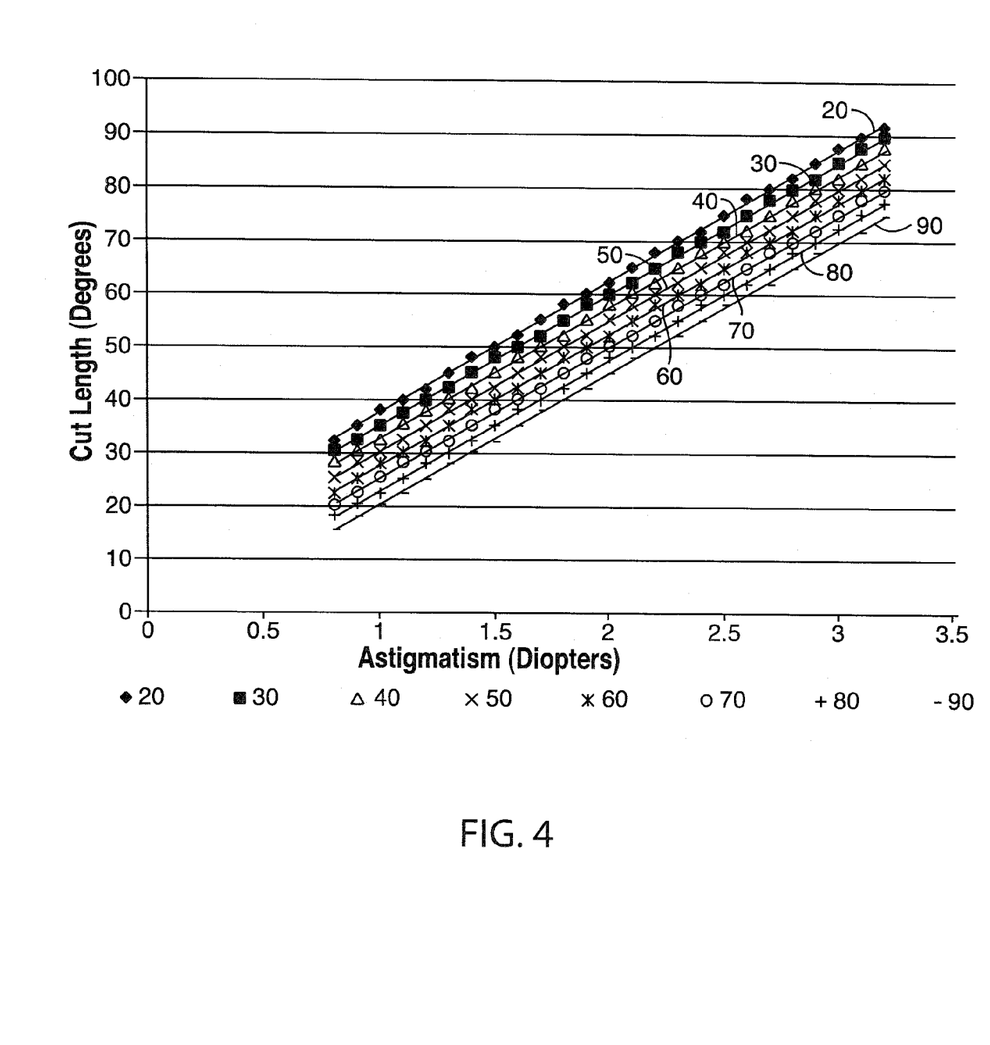
FIG. 4 provides a graph of the cut length (in degrees) based on the present astigmatism (in diopters) for patients in 8 different age ranges when performed in the 10 mm optical zone at 80% corneal depth.
Figure 5:
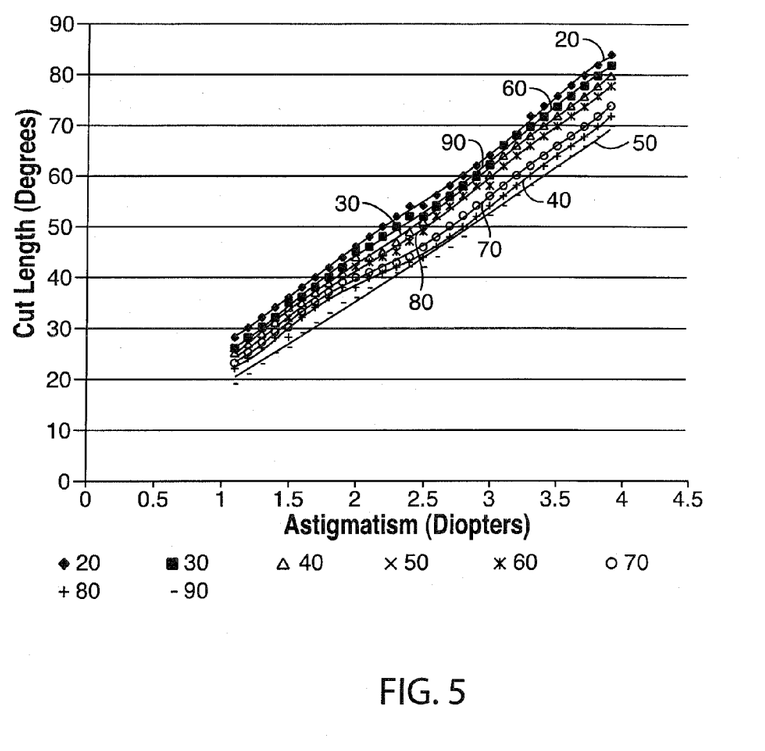
FIG. 5 provides a graph of the cut length (in degrees) based on the present astigmatism (in diopters) for patients in 8 different age ranges when performed in the 10 mm optical zone at 80% corneal depth.
Figure 6A:
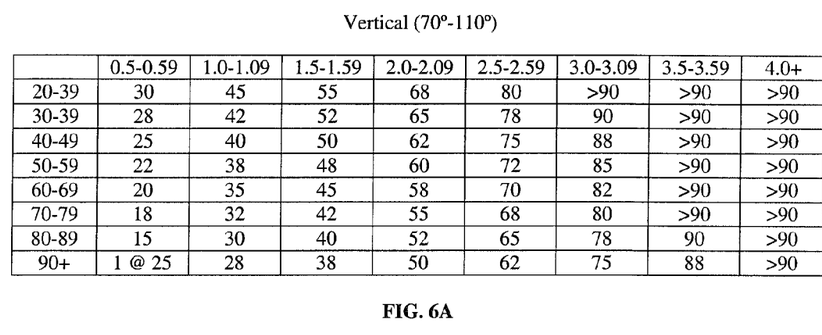
FIGS. 6A, 6B, and 6C are nomograms showing tables of cut lengths.
Figure 6B:
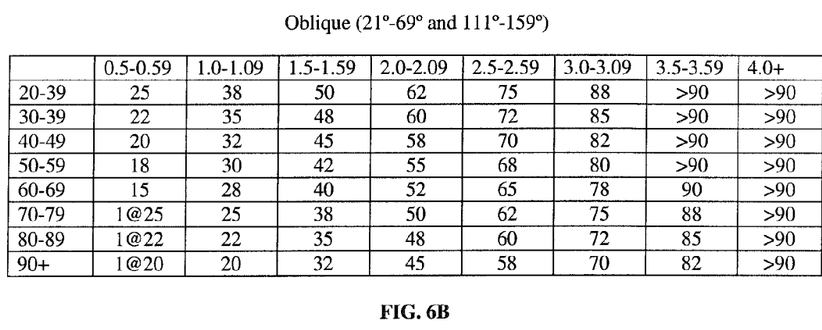
Figure 6C:
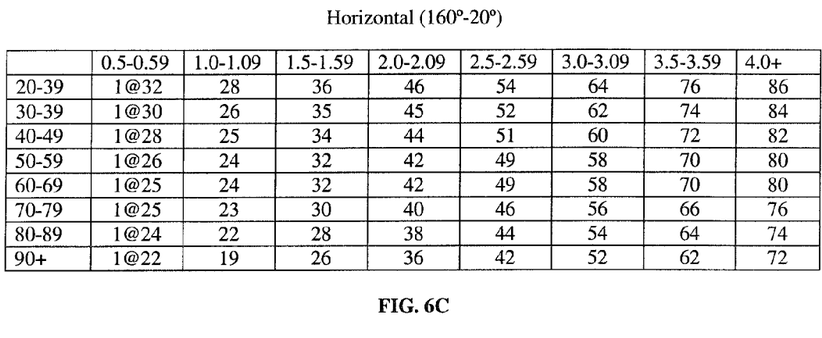

FIGS. 3-5 provide graphs of the relationship between different cuts (303) and (305). As the cuts are mirrored (the same size) the graphs simply provide on the vertical axis the length (in degrees) of both cuts (which are the same). It has been determined, as is visible in the graphs, that vertical and oblique astigmatisms allow for a very linear relationship between the prior variables. Specifically, there are linear relationships between the cut distance, the age, and the amount of correction desired. For horizontal astigmatisms, however, it has been determined that the relationships are much more complicated. FIG. 6 provides for some charts to show some exemplary values from the charts of FIGS. 3-5.

FIGS. 3-5 provide for graphs showing how to calculate the amount of a cut based on the three previously used variables. As discussed later, the graphs are preferably further modified by two to three additional variables as discussed. However, these variables provide for simple linear translation and their inclusion on the graphs of FIGS. 3-5 would be overly complicated. It should be recognized that while a specific mathematical formula can be used to provide the graphs of FIGS. 3-5 and the specific cuts (303) and (305), some degree of slop is actually still useful. For one, as accurate as the laser is, the eye itself is necessarily a slightly imperfect subject. Thus, a precise cut of 27.68° may be obtainable by the laser, but very small irregularities in the eye can render such precision cuts inaccurate. Further it is unlikely that a very small amount of variation made by a $1/100$ of a degree difference would even be detectable to the patient. Thus, values are generally rounded to the nearest degree.

The results of the graph of FIGS. 3-5 are provided by the performance of a number of specific procedures which are readily repeatable, and evaluation of the end performance. These procedures are then repeated and the amounts adjusted as additional information is learned.

As can be seen in FIG. 3, there are some general rules in the transition. FIG. 3 shows the cutting values for an astigmatism which is vertical (with-the-rule). The present case defines an astigmatism as vertical if it is from within 20° (inclusive) of the vertical position of the eye. As the vertical position (straight up) is defined as 90° (201), a vertical astigmatism is one between 70° and 110° inclusive in the coordinate system of FIG. 2.

As can be immediately seen from FIG. 3, the relationship between the three primary variables—age and astigmatism being the inputs and the cut length, in degrees being the output—is clearly linear. Specifically, for every about 0.2 diopters in increase in astigmatism, there will be an about 5° increase in cut length. This is a much shorter, and far more linear relationship, than was previously used for hand cutting and is illustrated by the clearly linear "best fit" curves of FIG. 3. Similarly, relationship to age is generally seen as being generally linear as well with an increase of about 20 years in age corresponding to a decrease of about 5° in cut. This is clearly visible by the regular spacing of the best-fit curves of FIG. 3 on the vertical axis which are for 8 different 10 year wide age categories (with the starting age for the group listed in the legend of FIG. 3). This relationship can be defined by the formula:

cut length=65°−(5°−$X$)+(5°−$Y$);

where $$X = \frac{\text{number of patient's age in years} - 30}{20};$$

and $$Y = \frac{\text{number of patient's astigmatism in diopters} - 2}{0.2}.$$

This linear relationship appears to be applicable for oblique astigmatism as well. That is, this would apply for an astigmatism that is more than 20° from horizontal or vertical or with an axis at 21°-69° or 111°-159° (depending on orientation). Thus, as can be seen for FIG. 4, every 0.2 diopters in increase in astigmatism results in an increase of about 5° in cut length and for an increase of about 20 years in age there is a decrease of about 5° in cut length.

The major difference between the vertical and oblique cuts is that an oblique cut essentially requires a reduction in cut length which is equivalent of a 0.2 diopter decrease in astigmatism (that is an essentially fixed 5° reduction simply for the astigmatism being oblique as opposed to vertical regardless of the actual position). This relationship can be defined by the formula:

cut length=60°−(5°−$X$)+(5°−$Y$);

where $$X = \frac{\text{number of patient's age in years} - 30}{20};$$

and $$Y = \frac{\text{number of patient's astigmatism in diopters} - 2}{0.2}.$$

Thus, the horizontal "shift" of the astigmatism results in virtually no change in the cut length relationship to known variables, and the orientation within the oblique range does not appear to matter. This relationship had not previously been known and most hand cut nomograms based the oblique cut length on a linear relationship with a horizontal astigmatism. This is clearly inaccurate based on FIG. 4.

As there is a linear relationship between the three factors, one can understand that a person of 20 with a 1.6 diopters of astigmatism in the vertical position would require two 58° cuts. Similarly, a person of 40 (decrease cut by 5°) with 2.0 diopters of astigmatism (increase cut by 10°) at an oblique angle (decrease by 5°) would also require two 58° cuts.

FIGS. 6A and 6B are charts with values for various cut lengths taken from the graphs of FIGS. 3 and 4. With this starting point, values not shown on FIGS. 6A and 6B can be determined using the graphs of FIGS. 3 and 4 and therefore any value can be mathematically determined.

With regards to horizontal astigmatism, the relationships are not linear with regards to any variables as can be seen in FIG. 5. In the horizontal astigmatism case, the variables appear to be significantly related and, as seen in FIG. 5, no easy conclusion between the relationship can be drawn as each line (as illustrated by the best fit curve) follows its own shape. There are, however, some visible trends. Specifically, the lines tend to be fairly "S" shaped which indicates that there are two different points of slope. Further, the regressions tend to become more linear at lower or higher ages. This latter effect is probably partially due to a lack of data at these points and, thus, the internal points are probably more accurately represented. As was indicated in the background section, cataracts tend to be more prevalent in populations aged 60-80. The three lines for these age ranges (the $2^{nd}$, $3^{rd}$, and $4^{th}$ lines from the bottom) tend to show a wave form or double bend. Implying that there is at least one additional variable influencing them.

Part of the reason that horizontal astigmatism correction is slightly more problematic is because of the access incision made by the surgeon to perform the underlying lens replacement. This necessarily provides another factor and it should be recognized that this will provide some of the variation and may account for all of it. However, prior nomograms, even when they take this into effect, have assumed a generally linear relationship and were often corrected by not providing a secondary cut because it was practically difficult for a human to place two cuts above each other on the same side of the eye. Thus, the correction of a hand cut nomogram was generally only on a single side of the eye and utilized the access correction for the remaining correction. In effect, it treated the access as one of its cuts, and then made the opposing one (which was obviously at a different depth, if done correctly). The present case, however, is capable of having two cuts at different areas (or end cutting on either side of a through-and-through incision) to utilize it.

As such, the surgical incision likely results in the first "S" bend (lower correction) slope. With a lower amount of astigmatism being present, the cuts will generally be more clustered as the surgical incision (301) will have a greater effect on the correction and less correction by the later cuts (305) and (303) is needed. In effect, as the surgeon's incision (301) is often around 30°, one can see how the cuts (303) and (305) are much closer, and of generally similar slope to each other in all three of the referenced lines up until an astigmatism of about 2 and a desired cut of around 30°.

Without being limited to any particular theory of operation, it is believed that this may be due to the incision (301) having primary impact at these values. As the astigmatism gets greater, however, this incision (which is often at a relatively fixed size) will become relatively less of the amount of cut needed and therefore the second slope (toward the right of FIG. 5) exists when the cut length is greater than 40° (or from 2-2.5 diopters of astigmatism). Again, it is believed that the cuts (303) and (305) become more important as the incision (301) has less effect than the cuts (303) and (305) when greater correction is needed. Thus, the charts show a horizontal shift in this area.

From the charts of FIG. 3-5 it should be apparent that the previously understood relationships of how to cut to correct astigmatisms are not suitable for use with more precise cutting instruments. Specifically, with a more precise cutting instrument, finer control of the length of cut is needed. Further, the cuts are generally much smaller than those done by hand in view of the greater accuracy (some can be almost half as small). This implies both that the prior nomograms did not correctly show the relationships, and, in fact, were likely inaccurate. Specifically, the present graphs generally illustrate a relationship of about 0.2 diopters, or 20 years of age indicating a 5° change in cut length. Prior hand cut nomograms did not even generally have a linear relationship with these variables, and to the extent that any portion of them was linear, they generally had a much different relationship.

While the ability to cut more accurate arcs and determine the values of the arcs is important, there is also a need to make sure that the inputs used to make the arcs are accurate. Because of this, there is provided a flowchart in FIG. 7 which provides for a method for evaluating an eye and determining its astigmatism. The chart in FIG. 7 is particularly valuable for determining the astigmatism, because the method of FIG. 7 was used in generating the graphs and tables of FIGS. 3-6 and, thus, use of similar tools can provide for more accurate input and reduce any systematic errors which are introduced through machine asymmetry.

Figure 7:
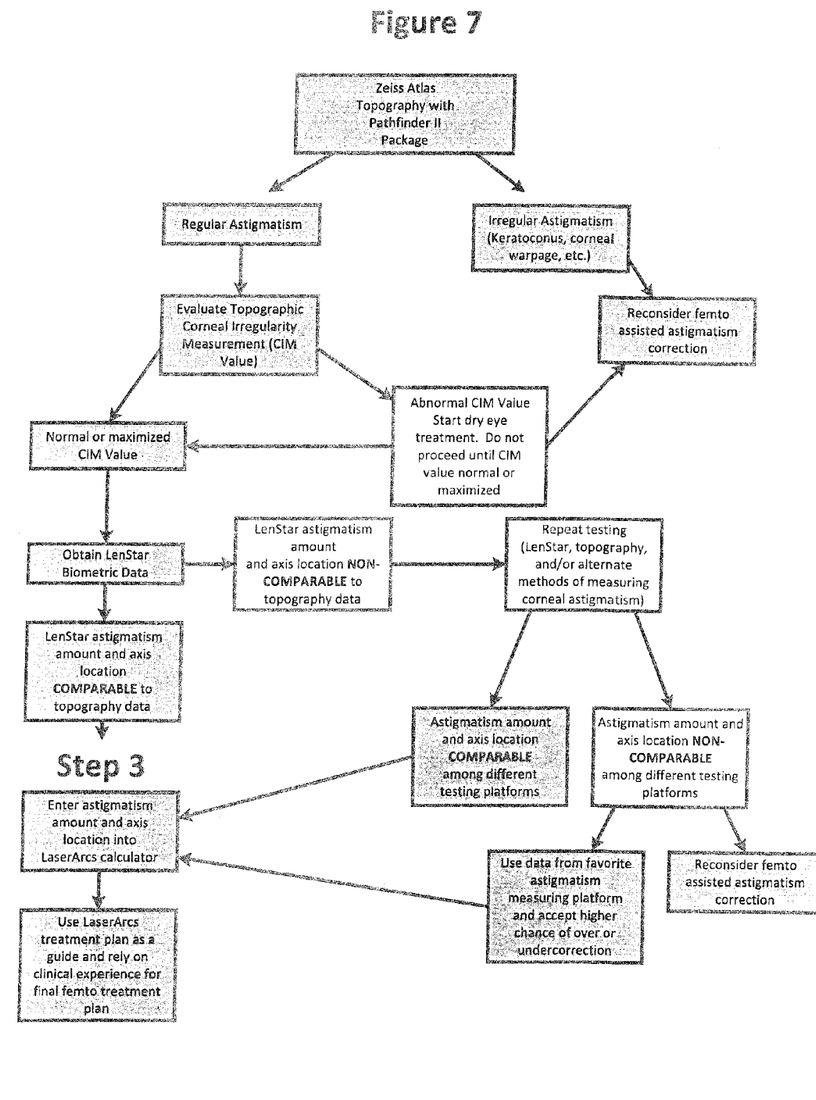
FIG. 7 is a flowchart for determining astigmatism amount and location.

In FIG. 7, the topography of the eye is first measured using a first system (701). In the depicted embodiment, this is performed using an ATLAS™ Corneal Topography System (Model 9000) available from Carl Zeiss Meditec. The ATLAS is running PathFinder™ II Corneal Analysis Software. This step is performed to look primarily for irregular astigmatism. If the result indicates that there is an irregular astigmatism (703) or other irregularity with the topography of the cornea, the course of treatment is reevaluated (709) as astigmatism correction may be difficult and inaccurate.

If the topography indicates only regular astigmatism (705), the topography Corneal Irregularity Measurement (CIM) value is determined (707). If this indicates a highly abnormal cornea, the assumption is that the patient's eyes are dry and a treatment of drops to provide moisture is provided (711). Once that treatment is completed, the measurement is retaken (711). If it is still irregular, again, the treatment is reconsidered (709).

If the results of the CIM either before or after dry eye treatment are normal (713), the patient is considered a candidate for astigmatism correction. However, before it is performed, a second method of topography is employed (715). In the embodiment of FIG. 7, this uses a LENSTAR LS 900® manufactured by Haag-Streit. Assuming the result of the second test (715) is comparable to the first (713) (the two methods reach matching conclusions) (721), it is accepted that the topography is accurate and the patient can obtain astigmatism correction. Thus, the common astigmatism value can be entered (731) into a calculator (such as that described in FIG. 8) to obtain a nomogram. In an embodiment, the values are automatically provided by the software of one or both of the topography systems to eliminate human error.

If the values are non-comparable (717), one or both methods will be retested (719) to determine if any error was inadvertently introduced. If the values are then comparable (723), the process proceeds as having now been verified and the values are entered into the calculator (731). If the values are not comparable (725), the process utilizes the treating surgeon's expertise. The surgeon may decide to abandon the astigmatism correction procedure (729) due to uncertainty in the effectiveness of treatment, or they may choose the data from their preferred platform, merge the data themselves, and/or utilize a third platform, to obtain a comfort level with the data they have (727). This data is then entered into the calculator (731). In an embodiment, this selection or averaging of data may not be performed by the surgeon, but may also be automated with the two topography systems making a determination about how to reconcile the data and passing that reconciliation on to the calculator (800).

Figure 8:
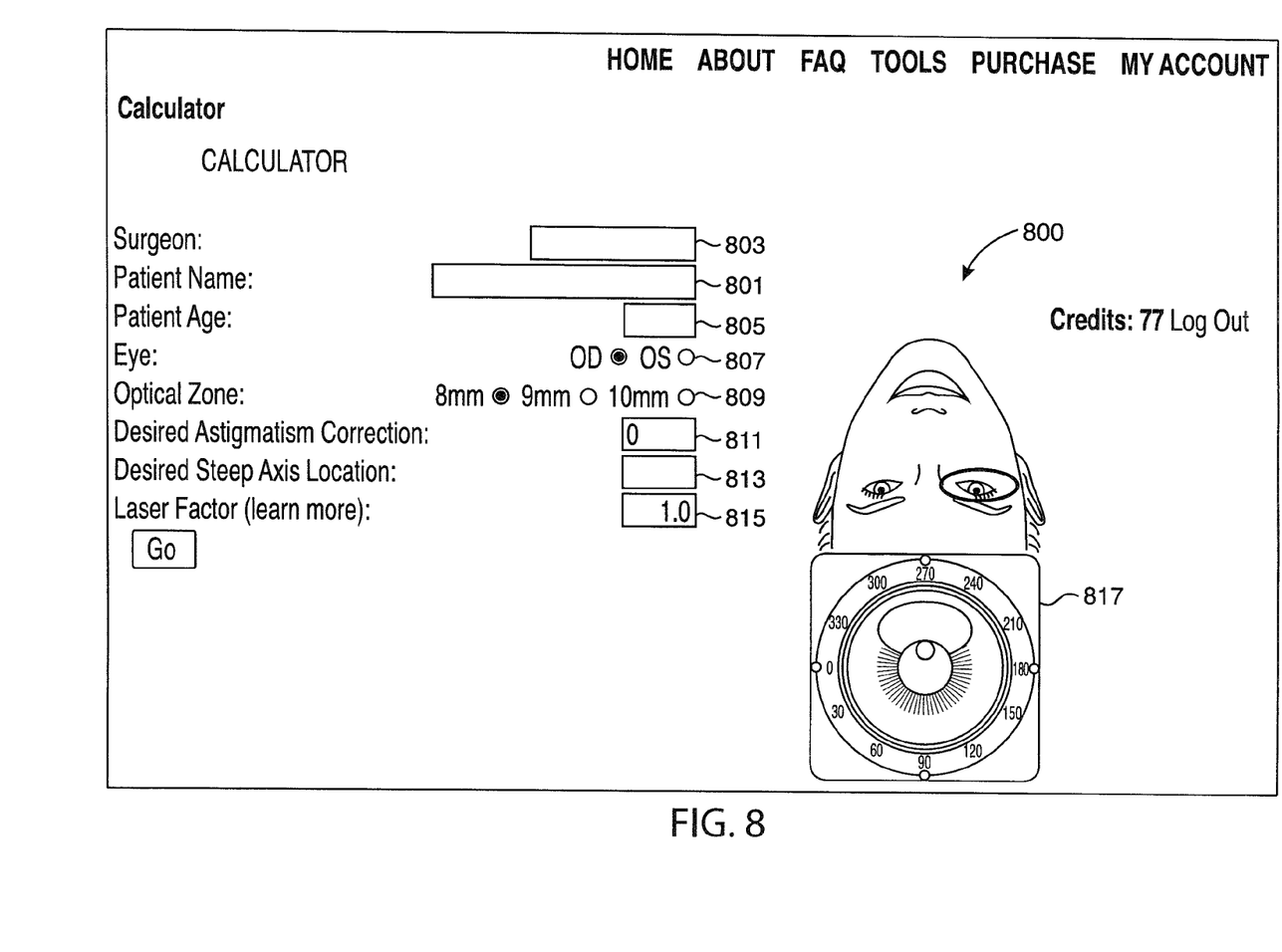
FIG. 8 is an embodiment of an entry system for a nomogram calculator.

In order to find the location and size of the cuts and provide a nomogram, there is provided a calculator (800) as in FIG. 8. In the embodiment of FIG. 8, the entry screen for the calculator (800) is provided as part of a webpage that can be accessed over a network (such as the Internet) by a doctor to obtain the desired information or may be accessed by licensed software functions such as by the topographic systems. The webpage includes the entry of various pieces of information.

The first pieces of information are identifiers for the patient (801) and/or doctor (803). These identifiers allow for the user of the calculator (800) to store, print, or otherwise associate the output of the system with a particular patient (801) to make sure that the correct procedure is associated with, and performed on, the correct patient (801). This information may be for human use, or may allow for machine identification of the patient (801) (such as by a machine readable code the patient (801) is provided with).

The new data point of entry is the patient's age (805). As the flexibility of the cornea changes with age (805), as discussed in conjunction with FIGS. 3-6, entry of the age (805) is desirable. The age (805) may be manually entered, or may be obtained from the topology software, an electronic medical record, or another source.

The next pieces of information describe the specifics of the astigmatism. Initially, entry of which eye the calculator is for (807). Specifics of the astigmatism of that eye include the desired correction (811) which will generally include the impact of an surgically induced astigmatism from the incision (301) and the angle (813). The angle (813) will serve to provide the basis of which graph or chart (FIGS. 3-6) is used to determine the cut length, as well as to position the cuts (303) and (305) relative to the eye (100) on the drawing (817). As discussed above, this information may be manually entered, or may be obtained from topology software.

The above, therefore, receives the standard information for making vision corrections. However, as opposed to in prior nomograms where this was all the information used, the present nomograms utilize a variety of additional information as the femtosecond laser allows for many more options in addition to providing more accurate cuts.

In the first, there is a determination of the optical zone (809) where the cut should be positioned. Traditionally, cuts (303) and (305) were always made at the 10 mm optical zone (10 mm from the pupillary center of the eye (100)). This location was chosen for a variety of reasons that were due to the nature of the hand cutting. Firstly, 10 mm is generally near the edge of the cornea (101). The further the cut is from the center of the eye the less likely it is to potentially impinge on vision. Thus, making the cuts (303) and (305) as far out as possible would generally result in the doctor having more slop to get slightly closer, without inadvertently impinging on the visual area. To put this another way, the further cut has more tolerance for error.

Secondly, the cuts (303) and (305) were made at this location because the cornea (101) is generally thicker at the edge of the eye (100). Thus, a slight miscalculation of the thickness of the cornea (101) was unlikely to lead to the blade cutting too deep (especially through the cornea (101)) which can result in complications. This second reason is particularly important. Even with the use of a guarded blade, a human can rarely cut a consistent depth (particularly when they are working on so small a structure) and a human also has trouble obtaining accurate measurements of the thickness of a cornea (101) at sufficient locations to be certain of its thickness at all points along the cutting path. Thus, the 10 mm optical location was used to provide for the potential slop and prevent problems.

This greater cut distance, however, has an impact. Specifically, the greater distance means that the cuts (305) and (303) must be longer to have the same reshaping effect. While this is a negative in that more of the cornea (101) needed to be cut it also allows for the surgeon to cut more accurately. This latter element may seem counter intuitive. However, when one considers that the cut was traditionally made by hand and therefore would have some error, the reason is clear. A longer cut has a greater error tolerance. For example, a cut of an additional mm can result in multiple degrees if additional cut length at a closer optical zone but only a single degree at a further optical zone. Thus, with the necessity of human slop, longer cuts allow for the actual cuts (305) and (303) to be within a better margin of error and provides for an amount of vision correction that is more within the target desired.

When a precision cutting instrument is used, however, this slop factor is not needed. While there is still a possibility of a closer cut impinging on the vision, the laser and associated computer control is much more capable of precisely positioning the cut at 9 mm or 8 mm as shown in selection (809). As the vision area is generally only 5-6 mm, it should be apparent that a precisely placed cut at 8 mm should not present a problem while a human being, attempting to cut at 8 mm could easily end up going close to 2 mm too far in and create a problem. While the present calculator only allows for cuts up to the 8 mm optical zone, in an alternative embodiment, this could extend to the 7 mm or even 6 mm optical zone.

The other advantage of the accuracy is that smaller cuts can have the same angular distance. Specifically, as an astigmatic cornea (100) is not hemispherical, but more paraboloid, a cut at a closer optical zone in the cornea (100) of the same actual length (e.g. in millimeters), has the same angular distance as a longer cut at a greater optical zone.

Selection of the location of the cut can be manual or can be performed by an interaction between the calculator, cutting tool controller, and topology software. In this embodiment, the topology software could, for example, select a cutting location that is more regular or that is based on the other size ratios of the eye (100). The laser could also assist by having current readings of the eye (100) (e.g. if the surgery was already ongoing) which could also include the already cut position of the incision (301).

Finally, there is an entry point for a laser factor (815). As the cutting instrument is very precise, the amount of the cut will be essentially the same in every procedure. However, the system cannot necessarily take into account the uniqueness of each device as compared to each other. Two identical lasers, in different physical locations, may produce slightly different cuts from each other, even though the cuts each makes are repeatedly accurate within the same laser to a very high degree. The laser factor allows a skilled surgeon to make adjustments based on information they already know about their laser. For example, if the surgeon knows that the cuts in their office always seem to slightly under correct based on the provided values to use, the laser factor allows the surgeon to put in a systematic alteration to correct all proposals by the same amount to attempt to eliminate this systemic alteration. Similarly, this factor could be selected by the tool control software to account for known uniqueness of the laser, or by the topology software or calculator to specifically take into account a known systemic variable such as use of different topology software.

Once these values are entered, the calculator (800) calculates the proposed cuts (303) and (305) and provides an indication of the cuts to be made, their positions, and their depth on image (817). While this information may be manually programmed into the tool controller of a precision cutting instrument, in a preferred embodiment the information is sent directly from the calculator (800) to the tool controller to allow the information to be obtained without the possibility of human error in its entry.

While not provided in the depicted embodiment, in a further embodiment the depth of the cut may also be selected. In the present embodiment, the values of FIGS. 3-6 are for a cut that is made 80% of the way through the cornea, ideally without cutting through the outer epidermal layer (which can eliminate much of the pain from eye surgery). It will be understood that the laser is capable of providing for an accurate cut at a fixed percentage of the cornea by measuring the thickness of the cornea as it cuts. It also will be understood that it is possible to alter this value in an embodiment, if desired. This would be particularly useful for small corrections where a cut of less than 80% would be desired to allow the cut to have enough length to result in come correction. However, cutting greater than 90% is generally not desired as cutting completely through can result in surgical complications and even with precision cutting, tissue failure when cut to very fine dimensions is still possible. Thus, 80% is chosen in the depicted embodiment as a value which allows for the vast majority of issues to be corrected, while still insuring that a full penetration of the cornea is prevented.

It should be recognized that in an embodiment of the present system, as discussed above, the nomogram may be generated by a computer calculator (800) as shown in FIG. 8 and then the nomogram information may be presented electronically, without entry by a human, to a precision cutting instrument, such as a femtosecond laser. As the laser is also controlled by a tool controller such as a computer, the computer may then simply instruct the laser to cut in accordance with the nomogram. This allows the entire cutting process to be performed without human intervention, if desired.

Still further, as the instruments to perform eye measurement can also be computer controlled, eye measurements, as shown in FIG. 7, can also be performed automatically with this information being fed into the calculator (800) automatically. This can result in what is essentially an entirely automated astigmatism correction procedure. In an embodiment, the surgeon would simply need to position the patient relative to the various machines and prepare them to undergo the surgery. Then the machines could handle the entire astigmatism correction surgery. This not only eliminates human slop in performing the procedure, but human error in determining how to perform it.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

It will further be understood that any of the ranges, values, or characteristics given for any single component of the present invention can be used interchangeably with any ranges, values, or characteristics given for any of the other components of the invention, where compatible, to form an embodiment having defined values for each of the components, as given herein throughout.

The invention claimed is:

1. A method of cutting cornea of an eye to correct astigmatism, the method comprising:
    providing a corneal topography system;
    providing a computer communicably coupled to said corneal topography system;
    determining an amount of astigmatism of said eye using said corneal topography system;
    determining an axis of said astigmatism of said eye using said corneal topography system;
    determining an age of said eye;
    selecting a mirrored cut position in said cornea using said computer, said cut position being less than a 10 mm optical zone and greater than a 6 mm optical zone and comprising two cuts on opposing sides of said eye, said optical zones being measured radially from a pupillary center of said eye;
    receiving said amount and said axis on said computer from said corneal topography system;
    calculating an arcuate cut length from said amount and said age based on cut positions including:
        determining, with said computer, that said axis is greater than 20° from vertical and horizontal axis of said eye; and
        calculating, with said computer, the cut length using a first formula:

cut length=60°−(5°·X)+(5°·Y);
    where $$X = \frac{\text{number of patient's age in years} - 30}{20};$$

and $$Y = \frac{\text{number of patient's astigmatism in diopters} - 2}{0.2};$$

or,
    determining, with said computer, that said axis is less than or equal to 20° from vertical axis of said eye; and
    calculating, with said computer, the cut length using a second formula:

cut length=65°−(5°·X)+(5°·Y);
    where $$X = \frac{\text{number of patient's age in years} - 30}{20};$$

and $$Y = \frac{\text{number of patient's astigmatism in diopters} - 2}{0.2};$$

and
    utilizing a femtosecond laser to cut said cut length at said cut position.

2. The method of claim 1, wherein said cut position is greater than an 8 mm optical zone.

3. The method of claim 1, wherein said cut position is at an optical zone being measured about 8 mm radially from the pupillary center of said eye.

4. The method of claim 1, wherein said cut position is at an optical zone being measured about 9 mm radially from the pupillary center of said eye.

5. The method of claim 1, wherein said cut position is at an optical zone being measured between 8 mm and 9 mm radially from the pupillary center of said eye.

6. The method of claim 1, wherein said cut position is at an optical zone being measured between 9 mm and 10 mm radially from the pupillary center of said eye.

7. The method of claim 1, wherein said cut length is between 15° and 90°.

8. A method of cutting cornea of an eye to correct astigmatism, the method comprising:
    providing a corneal topography system;
    providing a computer communicably coupled to said corneal topography system;
    determining an amount of astigmatism of said eye using said corneal topography system;
    determining an axis of said astigmatism of said eye using said corneal topography system;
    determining an age of said eye;
    selecting a cut position in said cornea using said computer;
    receiving said amount and said axis on said computer from said corneal topography system;
    calculating an arcuate cut length from said amount and said age based on cut positions including:
        determining, with said computer, that said axis is greater than 20° from vertical and horizontal axis of said eye; and
        calculating, with said computer, the cut length using a first formula:

cut length=60°−(5°−X)+(5°−Y);
    where $$X = \frac{\text{number of patient's age in years} - 30}{20};$$

and $$Y = \frac{\text{number of patient's astigmatism in diopters} - 2}{0.2};$$

and
    utilizing a femtosecond laser to cut said cut length at said cut position.

9. The method of claim 8, wherein said cut is one of a pair of mirrored cuts on opposing sides of said eye.

10. The method of claim 8, wherein said cut length is between 15° and 90°.

11. A method of cutting cornea of an eye to correct astigmatism, the method comprising:
   providing a corneal topography system;
   providing a computer communicably coupled to said corneal topography system;
   determining an amount of astigmatism of said eye using said corneal topography system;
   determining an axis of said astigmatism of said eye using said corneal topography system;
   determining an age of said eye;
   selecting a cut position in said cornea using said computer;
   receiving said amount and said axis on said computer from said corneal topography system;
   calculating an arcuate cut length from said amount and said age based on cut positions including:
      determining, with said computer, that said axis is no more than 20° from vertical axis of said eye; and
      calculating, with said computer, the cut length using a second formula:
         cut length=65°−(5°−$X$)+(5°−$Y$);
      where
         $$X = \frac{\text{number of patient's age in years} - 30}{20};$$
      and
         $$Y = \frac{\text{number of patient's astigmatism in diopters} - 2}{0.2};$$
      and
   utilizing a femtosecond laser to cut said cut length at said cut position.

12. The method of claim 11, wherein said cut is one of a pair of mirrored cuts on opposing sides of said eye.

13. The method of claim 11, wherein said cut length is between 15° and 90°.

* * * * *